(12) United States Patent
Khile et al.

(10) Patent No.: US 8,859,769 B2
(45) Date of Patent: Oct. 14, 2014

(54) PROCESSES FOR PREPARING TICAGRELOR INTERMEDIATE, 4,6-DICHLORO-5-NITRO-2-(PROPYLTHIO)PYRIMIDINE

(75) Inventors: Anil Shahaji Khile, Navi Mumbai (IN); Jayesh Patel, Banaskhantha (IN); Nikhil Trivedi, Navimumbai (IN); Nitin Sharadchandra Pradhan, Thane (West) (IN)

(73) Assignee: Actavis Group PTC EHF (IS)

( * ) Notice: Subject to any disclaimer, the term of this patent is extended or adjusted under 35 U.S.C. 154(b) by 134 days.

(21) Appl. No.: 13/521,780

(22) PCT Filed: Feb. 15, 2011

(86) PCT No.: PCT/IB2011/000459
§ 371 (c)(1),
(2), (4) Date: Jul. 12, 2012

(87) PCT Pub. No.: WO2011/101740
PCT Pub. Date: Aug. 25, 2011

(65) Prior Publication Data
US 2013/0030176 A1    Jan. 31, 2013

(30) Foreign Application Priority Data

Feb. 16, 2010    (IN) .............................. 391/CHE/2010
Aug. 30, 2010    (IN) .......................... 2501/CHE/2010

(51) Int. Cl.
*C07D 239/38*    (2006.01)
*C07D 239/60*    (2006.01)
*C07D 487/04*    (2006.01)
*C07D 239/47*    (2006.01)

(52) U.S. Cl.
CPC ............ *C07D 239/47* (2013.01); *C07D 487/04* (2013.01); *C07D 239/60* (2013.01)
USPC ............................. 544/299; 544/315; 544/316

(58) Field of Classification Search
CPC ............................. C07D 239/38; C07D 239/60
USPC .......................................... 544/299, 315, 316
See application file for complete search history.

(56) References Cited

U.S. PATENT DOCUMENTS

| | | | |
|---|---|---|---|
| 5,082,968 A * | 1/1992 | Brunelle ........................ | 564/240 |
| 5,274,093 A | 12/1993 | Feld | |
| 5,654,285 A | 8/1997 | Ingall et al. | |
| 5,747,496 A | 5/1998 | Cox et al. | |
| 6,156,756 A | 12/2000 | Hardern et al. | |
| 6,251,910 B1 | 6/2001 | Guile et al. | |
| 6,525,060 B1 | 2/2003 | Hardern et al. | |
| 6,974,868 B2 | 12/2005 | Hardern et al. | |
| 7,067,663 B2 | 6/2006 | Larsson et al. | |
| 7,250,419 B2 | 7/2007 | Hardern et al. | |
| 2007/0265282 A1 | 11/2007 | Hardern et al. | |
| 2008/0214812 A1 | 9/2008 | Hardern et al. | |

FOREIGN PATENT DOCUMENTS

| | | |
|---|---|---|
| EP | 0996621 B1 | 10/2003 |
| EP | 1135391 B1 | 3/2004 |
| WO | 0192263 A1 | 12/2001 |
| WO | 2008018823 A1 | 2/2008 |
| WO | 2010030224 A1 | 3/2010 |
| WO | 2011017108 A2 | 2/2011 |

OTHER PUBLICATIONS

Herriott et al.; "Phase Transfer Catalysis. An Evaluation of Catalysts"; Journal of the American Chemical Society; 97(9); pp. 2345-2349; (1975).
EP Application No. 11 712 669.8; filed Oct. 31, 2013; office action issued Oct. 31, 2013; 4 pages.
International Search Report and Written Opinion; International Application No. PCT/IB2011/000459; International Filing Date Feb. 15, 2011; Date of Mailing May 24, 2011; Applicant's File Reference No. ADC0048US; 13 pages.
McGraw-Hill Dictionary of Chemistry; Sybil P. Parker Editor in Chief, New York, pp. 40, 78, 267, 293; (1997).
2-Thiobarbituric acid, Product Specification of SIGMA-ALDRICH retrieved from the internet www.sigmaaldrich.com/ .. Jsigmaaldrich/ .. ./Sigma-Aidric . . . • Sigma-Aldrich • 2• Thiobarbituric acid. Product No. T 5500. Storage Temperature RT. Product Description. Molecular Formula: C4H4N2O2S. Molecular Weight: 144.2; printed May 2015.

* cited by examiner

*Primary Examiner* — Deepak Rao
(74) *Attorney, Agent, or Firm* — Cantor Colburn LLP

(57) ABSTRACT

Provided herein are improved, commercially viable and industrially advantageous processes for the preparation of a substantially pure ticagrelor intermediate, 4,6-dichloro-5-nitro-2-(propylthio)pyrimidine, Formula (II). The intermediate is useful for preparing ticagrelor, or a pharmaceutically acceptable salt thereof in high yield and purity.

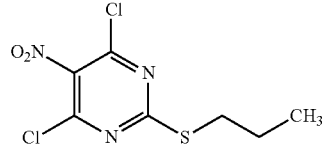

(II)

16 Claims, No Drawings

PROCESSES FOR PREPARING TICAGRELOR INTERMEDIATE, 4,6-DICHLORO-5-NITRO-2-(PROPYLTHIO)PYRIMIDINE

CROSS-REFERENCE TO RELATED APPLICATIONS

This application is a 371 of PCT/IB2011/000459, filed Feb. 15, 2011, which claims the benefit of priority to Indian provisional application Nos. 391/CHE/2010, filed on Feb. 16, 2010; and 2501/CHE/2010, filed on Aug. 30, 2010, under the provisions of 35 U.S.C. 119 and the International Convention for the protection of Industrial Property, which are incorporated herein by reference in their entirety.

FIELD OF THE DISCLOSURE

The present disclosure relates to improved, commercially viable and industrially advantageous processes for the preparation of a substantially pure ticagrelor intermediate, 4,6-dichloro-5-nitro-2-(propylthio)pyrimidine. The intermediate is useful for preparing ticagrelor, or a pharmaceutically acceptable salt thereof, in high yield and purity.

BACKGROUND

U.S. Pat. Nos. 6,251,910 and 6,525,060 disclose a variety of triazolo[4,5-d]pyrimidine derivatives, processes for their preparation, pharmaceutical compositions comprising the derivatives, and method of use thereof. These compounds act as $P_{2T}$ ($P2Y_{ADP}$ or $P2T_{AC}$) receptor antagonists and they are indicated for use in therapy as inhibitors of platelet activation, aggregation and degranulation, promoters of platelet disaggregation and anti-thrombotic agents. Among them, Ticagrelor, [1S-(1α,2α,3β(1S*,2R*),5β)]-3-[7-[2-(3,4-difluorophenyl)cyclopropyl]amino]-5-(propylthio)-3H-1,2,3-triazolo[4,5-d]pyrimidin-3-yl)-5-(2-hydroxyethoxy)-cyclopentane-1,2-diol, acts as Adenosine uptake inhibitor, Platelet aggregation inhibitor, P2Y12 purinoceptor antagonist and Coagulation inhibitor. It is indicated for the treatment of thrombosis, angina, Ischemic heart diseases and coronary artery diseases. Ticagrelor is represented by the following structural formula I:

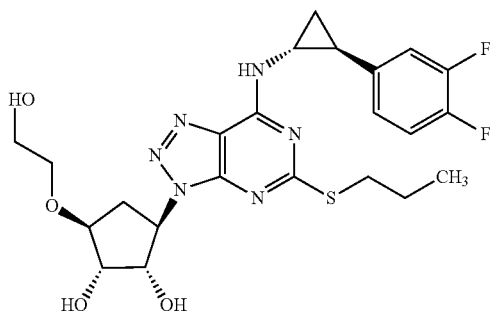

I

Ticagrelor is the first reversibly binding oral adenosine diphosphate (ADP) receptor antagonist and is chemically distinct from thienopyridine compounds like clopidogrel. It selectively inhibits P2Y12, a key target receptor for ADP. ADP receptor blockade inhibits the action of platelets in the blood, reducing recurrent thrombotic events. The drug has shown a statistically significant primary efficacy against the widely prescribed clopidogrel (Plavix) in the prevention of cardiovascular (CV) events including myocardial infarction (heart attacks), stroke, and cardiovascular death in patients with ACS.

Various processes for the preparation of ticagrelor, its enantiomers and related compounds, and their pharmaceutically acceptable salts are disclosed in U.S. Pat. Nos. 6,251,910; 6,525,060; 6,974,868; 7,067,663; and 7,250,419; U.S. Patent application Nos. 2007/0265282 and 2008/0214812; and European Patent Nos. EP0996621 and EP1135391; and PCT Publication Nos. WO2008/018823 and WO2010/030224.

In the preparation of ticagrelor or a pharmaceutically acceptable salt thereof, 4,6-dichloro-5-nitro-2-(propylthio)pyrimidine of formula II:

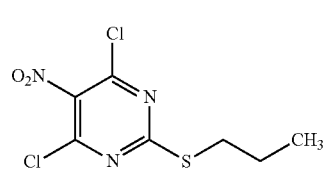

II is a key intermediate. According to U.S. Pat. No. 5,654,285, the 4,6-dichloro-5-nitro-2-(propylthio)pyrimidine of formula II is prepared by adding propyl iodide to a solution of 4,6-dihydroxy-2-mercaptopyrimidine in potassium hydroxide; the resulting mixture is stirred for 4 days followed by acidifying the solution to pH 2-3 to produce 2-propylthio-pyrimidine-4,6-diol; which is then reacted with excess fuming nitric acid to produce 5-nitro-2-propylthiopyrimidine-4,6-diol. The 5-nitro-2-propylthiopyrimidine-4,6-diol is reacted with phosphoryl chloride in the presence of N,N-diethylaniline at reflux to produce a reaction mass, followed by concentrating to half volume and pouring onto ice to yield a black tar. The tar is extracted with ether to afford a solution, which is then dried and evaporated. The residue is chromatographed (SiO2, light petrol) to produce 4,6-dichloro-5-nitro-2-(propylthio)pyrimidine.

According to U.S. Pat. No. 5,747,496, the 4,6-dichloro-5-nitro-2-(propylthio)pyrimidine of formula II is prepared by adding propyl iodide to a suspension of 4,6-dihydroxy-2-mercaptopyrimidine in water containing sodium hydroxide; the reaction mixture is stirred for 2 weeks and then the reaction mass is concentrated to half volume; followed by the addition of hydrochloric acid and isolating the product by filtration to produce 2-propylthio-pyrimidine-4,6-diol. The 2-propylthio-pyrimidine-4,6-diol is then reacted with excess fuming nitric acid to produce 5-nitro-2-propylthiopyrimidine-4,6-diol. The 5-nitro-2-propylthiopyrimidine-4,6-diol is reacted with phosphoryl chloride in the presence of N,N-dimethylaniline at reflux to produce a reaction mass. The cooled reaction mass is poured onto ice followed by extracting with diethyl ether to afford a solution; then the combined extracts are dried and concentrated. The residue is chromatographed (SiO2, light petrol) to produce 4,6-dichloro-5-nitro-2-(propylthio)pyrimidine.

According to U.S. Pat. No. 6,525,060, ticagrelor is prepared by the condensation of 4,6-dichloro-5-nitro-2-(propylthio)pyrimidine with [3aR-(3aα,4α,6α,6aα)]-6-amino-tetrahydro-2,2-dimethyl-4H-cyclopenta-1,3-dioxol-4-ol, hydrochloride salt in the presence of N,N-diisopropylethylamine in tetrahydrofuran to produce [3aR-(3aα,4α,6α, 6aα)]-6-[[6-chloro-5-nitro-2-(propylthio)-pyrimidin-4-yl]amino]-tetrahydro-2,2-dimethyl-4H-cyclopenta-1,3-dioxol-4-ol, followed by reduction in the presence of iron powder in acetic acid to produce [3aR-(3aα,4α,6α,6aα)]-6-[[5-amino-6-chloro-2-(propylthio)-pyrimidin-4-yl]amino]-tetrahydro-2,2-dimethyl-4H-cyclopenta-1,3-dioxol-4-ol, which is then reacted with isoamyl nitrite in acetonitrile to produce [3aR-(3aα,4α,6α,6aα)]-6-[7-chloro-5-(propylthio)-3H-1,2,3-triazolo[4,5-d]-pyrimidin-3-yl]tetrahydro-2,2-dimethyl-4H-cyclopenta-1,3-dioxol-4-ol. The resulting triazolo[4,5-d]-pyrimidin compound is reacted with ammonia in tetrahydrofuran to produce [3aR-(3aα,4α,6α,6aα)]-6-[7-amino-5-(propylthio)-3H-1,2,3-triazolo[4,5-d]-pyrimidin-3-yl]tetrahydro-2,2-dimethyl-4H-cyclopenta-1,3-dioxol-4-ol, which is then reacted with a solution of trifluoromethane-sulfonyloxy-acetic acid methyl ester in tetrahydrofuran in the presence of butyllithium to produce [3aR-(3aα,4α,6α,6aα)]-6-[[7-amino-5-(propylthio)-3H-1,2,3-triazolo[4,5-d]-pyrimidin-3-yl]tetrahydro-2,2-dimethyl-4H-cyclopenta-1,3-dioxol-4-ol]oxy]acetic acid methyl ester, followed by bromination in the presence of isoamylnitrite in bromoform to produce [3aR-(3aα,4α,6α,6aα)]-6-[[7-bromo-5-(propylthio)-3H-1,2,3-triazolo[4,5-d]-pyrimidin-3-yl]tetrahydro-2,2-dimethyl-4H-cyclopenta-1,3-dioxol-4-ol]oxy]acetic acid methyl ester. The resulting bromo compound is then reacted with (1R-trans)-2-(3,4-difluorophenyl)cyclopropanamine [R—(R*,R*)]-2,3-dihydroxybutanedioate (1:1) salt in the presence of N,N-diisopropylethylamine in dichloromethane to produce [3aR-[3aα,4α,6α(1R*,2S*),6aα]]-[[6-[7-[[2-(3,4-difluorophenyl)cyclopropyl]amino]-5-(propylthio)-3H-1,2,3-triazolo[4,5-d]-pyrimidin-3-yl]tetrahydro-2,2-dimethyl-4H-cyclopenta-1,3-dioxol-4-ol]oxy]acetic acid methyl ester, followed by reaction with DIBAL-H in tetrahydrofuran to produce [3aR-[3aα,4α,6α(1R*,2S*),6aα]]-[[6-[7-[[2-(3,4-difluorophenyl)cyclopropyl]amino]-5-(propylthio)-3H-1,2,3-triazolo[4,5-d]-pyrimidin-3-yl]tetrahydro-2,2-dimethyl-4H-cyclopenta-1,3-dioxol-4-ol]oxy]-ethanol, which is then treated with trifluoroacetic acid in water to produce [1S-(1α,2α,3β(1S*,2R*),5β)]-3-[7-[2-(3,4-difluorophenyl)cyclopropyl]amino]-5-(propylthio)-3H-1,2,3-triazolo[4,5-d]pyrimidin-3-yl]-5-(2-hydroxyethoxy)-cyclopentane-1,2-diol (ticagrelor).

The processes for the preparation of 4,6-dichloro-5-nitro-2-(propylthio)pyrimidine of formula II disclosed in the above mentioned prior art have the following disadvantages and limitations:

a) longer reaction times, low yields and low purities of the products;
b) the time required for the alkylation reaction is from about 4 days to about 2 weeks, which is industrially not feasible;
c) the alkylation reaction reported in the prior art results in low yields and low purity of the product;
d) the use of excess nitric acid leads to the formation of nitration products;
e) the purity of the 5-nitro-2-propylthiopyrimidine-4,6-diol obtained in nitration is low and the color of the product is very dark;
f) the processes require large volumes of water to quench excess nitric acid on an industrial scale;
g) the processes involve the use of excess phosphorus oxychloride in the chlorination reaction;
h) the processes involve the use of N,N-dimethyl or N,N-diethyl aniline in the chlorination reaction, which are toxic and dangerous to environment; and
i) the overall process generates a large quantity of chemical waste which is difficult to treat.

Based on the aforementioned drawbacks, the prior art processes have been found to be unsuitable for the preparation of 4,6-dichloro-5-nitro-2-(propylthio)pyrimidine of formula II at lab scale and in commercial scale operations.

A need remains for an improved and commercially viable process of preparing 4,6-dichloro-5-nitro-2-(propylthio)pyrimidine of formula II with high yields and purity, to resolve the problems associated with the processes described in the prior art, and that will be suitable for large-scale preparation. Desirable process properties include non-hazardous conditions, environmentally friendly and easy to handle reagents, reduced reaction times, reduced cost, greater simplicity, increased purity, and increased yield of the product, thereby enabling the production of Ticagrelor and its pharmaceutically acceptable acid addition salts in high purity and in high yield.

SUMMARY

The present inventors have surprisingly found that the ticagrelor intermediate, 4,6-dichloro-5-nitro-2-(propylthio) pyrimidine of formula II can be prepared, with reduced reaction times, in high purity, and with high yield, either i) by reacting 4,6-dihydroxy-2-mercaptopyrimidine (also known as 2-thiobarbituric acid) with an alkylating agent, preferably propyl halide, in the presence of a base and a phase transfer catalyst in a reaction inert solvent; or ii) by reacting an alkali metal salt of 4,6-dihydroxy-2-mercaptopyrimidine with an alkylating agent, preferably propyl halide, in the presence of a base, optionally in the presence of a phase transfer catalyst, in a reaction inert solvent; to produce a reaction mass, followed by acidification with an acid to produce 2-propylthio-pyrimidine-4,6-diol, which is then subjected to a nitration reaction with fuming nitric acid in the presence of acetic acid to produce 5-nitro-2-propylthiopyrimidine-4,6-diol, which is then chlorinated with a suitable chlorinating agent in the presence of an aliphatic organic base to produce 4,6-dichloro-5-nitro-2-(propylthio)pyrimidine.

Based on the extensive research and experimentation carried out by the present inventors, it has been surprisingly and unexpectedly found that the use of an alkali metal salt of 2-thiobarbituric acid as a starting material, instead of 2-thiobarbituric acid, avoids the use of lengthy, tedious and cumbersome procedures like the use of additional and hazardous solvents, prolonged reaction time periods such as from about 4 days to about 2 weeks, additional reagents like phase transfer catalysts, multiple crystallizations and/or isolation steps, column chromatographic purifications, repeated washings with solvents like cyclohexane; and thereby producing the alkylated product with higher and consistent yields and thus making the process simple, convenient and cost effective. The alkali metal salt of 2-thiobarbituric acid can be conveniently prepared with high purity (greater than 99.5% pure), just prior to use in the preparation of 2-propylthio-pyrimidine-4,6-diol, by reacting dimethyl malonate with thiourea in the presence of sodium methoxide in a suitable solvent under appropriate conditions.

It has been found that the alkylation reaction can also be conveniently and successfully carried out by using less expensive alkylating agent 'propyl bromide' instead of the highly expensive 'propyl iodide' when the alkali metal salt of 2-thiobarbituric acid is used as a starting material instead of 2-thiobarbituric acid.

In one aspect, provided herein is an efficient, convenient, commercially viable and environment friendly process for the preparation of pure ticagrelor intermediate, 4,6-dichloro-5-nitro-2-(propylthio)pyrimidine of formula II. Advantageously, the reagents used for present invention are less hazardous and easy to handle at a commercial scale, and the process involves shorter reaction times than the prior art processes.

In another aspect, the present invention provides 4,6-dichloro-5-nitro-2-(propylthio)pyrimidine of formula II having purity greater than about 95%, specifically greater than about 98%, more specifically greater than about 99%, and most specifically greater than about 99% measured by HPLC.

In still another aspect, the present invention also encompasses the use of pure 4,6-dichloro-5-nitro-2-(propylthio)pyrimidine of formula II obtained by the process disclosed herein for preparing ticagrelor.

The process for the preparation of 4,6-dichloro-5-nitro-2-(propylthio)pyrimidine of formula II disclosed herein has the following advantages over the processes described in the prior art:

1) the alkylation reaction is completed with in 30 to 35 hours;
2) the color of the alkylated product (2-propylthio-pyrimidine-4,6-diol) obtained is improved;
3) the yield and purity of the alkylated product is increased;
4) the process disclosed herein is also carried out by employing propyl bromide as the alkylating agent in the alkylation reaction, which is a much cheaper raw material when compared with propyl iodide, which is used in the prior art processes, thereby making the process cost effective and commercially viable;
5) the amount of nitric acid used for the nitration reaction is minimized with the modification of reaction conditions, thereby reducing the acidic waste produced and avoiding the formation of over nitrated by-products;
6) the quality of nitration product (5-nitro-2-propylthiopyrimidine-4,6-diol) obtained is improved;
7) a reduced (minimized) quantity of phosphorus oxychloride is used for the chlorination reaction and the excess is distilled off for recycling purposes, which reduces the chlorinated waste;
8) the use of hazardous aromatic organic bases like N,N-dimethylaniline and N,N-diethyl aniline in the chlorination reaction is avoided and replaced by aliphatic tertiary amine bases; and
9) the overall process time is shortened, the overall yield and purities are increased, there is a reduction in chemical waste, and the process avoids the use of hazardous chemicals.

DETAILED DESCRIPTION

According to one aspect, there is provided a process for preparing ticagrelor intermediate, 4,6-dichloro-5-nitro-2-(propylthio)pyrimidine of formula II:

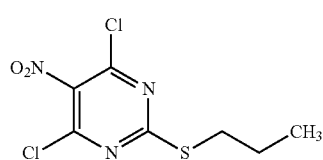

comprising:
a) reacting 2-thiobarbituric acid of formula V:

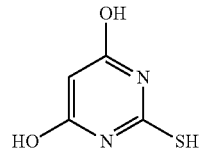

with an alkylating agent of formula VI:

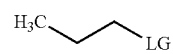

wherein LG is a leaving group selected from OH, Cl, Br, I, $OSO_3$ alkyl or aryl, $OCOCH_3$ and $OP(O-alkyl)_3$;
in the presence of a phase transfer catalyst and a base in a first solvent to produce 2-propylthio-pyrimidine-4,6-diol of formula IV:

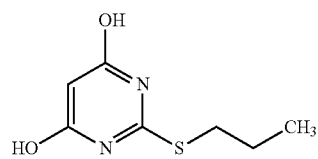

(or)
reacting an alkali metal salt of 2-thiobarbituric acid of formula V with the alkylating agent of formula VI in the presence of a base, optionally in the presence of a phase transfer catalyst, in the first solvent to produce the 2-propylthio-pyrimidine-4,6-diol of formula IV;
b) nitrating the compound of formula IV with a nitrating agent in a second solvent to produce 5-nitro-2-propylthiopyrimidine-4,6-diol of formula III:

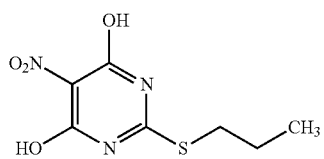

c) chlorinating the compound of formula III with a chlorinating agent in the presence of an aliphatic organic base, optionally in the presence of a third solvent, to produce substantially pure 4,6-dichloro-5-nitro-2-(propylthio)pyrimidine of formula II.

The term "substantially pure 4,6-dichloro-5-nitro-2-(propylthio)pyrimidine" refers to 4,6-dichloro-5-nitro-2-(propylthio)pyrimidine having a total purity of greater than about 95%, specifically greater than about 98%, more specifically greater than about 99%, and still more specifically greater than about 99.5%. The purity is preferably measured by High Performance Liquid Chromatography (HPLC). For example, the purity of 4,6-dichloro-5-nitro-2-(propylthio)pyrimidine obtained by the process disclosed herein is about 95% to about 99%, or about 98% to about 99.5%, as measured by HPLC.

In one embodiment, the leaving group 'LG' in the compound of formula VI is OH, Cl, Br or I; specifically the leaving group is Br or I; and a most specific leaving group is Br.

Specifically the alkylating agent of formula VI used in step-(a) is n-propyl bromide or n-propyl iodide; and a most specific alkylating agent is n-propyl bromide.

In another embodiment, the alkali metal salt of 2-thiobarbituric acid of formula V used in step-(a) is sodium 2-thiobarbiturate or potassium 2-thiobarbiturate; and most specifically sodium 2-thiobarbiturate.

Exemplary first solvents used in step-(a) include, but are not limited to, water, an alcohol, a ketone, a $C_1$ to $C_3$ aliphatic amide, a $C_2$ to $C_5$ aliphatic nitrile, an ether, a hydrocarbon solvent, a polar aprotic solvent, and mixtures thereof. The term solvent also includes mixtures of solvents.

In one embodiment, the first solvent is selected from the group consisting of water, methanol, ethanol, n-propanol, isopropanol, n-butanol, isobutanol, tert-butanol, amyl alcohol, hexanol, acetone, methylethyl ketone, methylisobutyl ketone, methyl tert-butyl ketone, acetonitrile, tetrahydrofuran, dioxane, diethyl ether, diisopropyl ether, monoglyme, diglyme, n-pentane, n-hexane, n-heptane, cyclohexane, toluene, xylene, N,N-dimethylformamide, N,N-dimethylacetamide, dimethylsulfoxide, and mixtures thereof; more specifically, the first solvent is selected from the group consisting of water, methanol, ethanol, n-propanol, isopropanol, and mixtures thereof; and most specifically a mixture of water and methanol.

Exemplary phase transfer catalysts suitable for facilitating the alkylation reaction in step-(a) include, but are not limited to, quaternary ammonium salts substituted with a group such as a straight or branched alkyl group having 1 to about 18 carbon atoms, a phenyl lower alkyl group including a straight or branched alkyl group having 1 to 6 carbon atoms which is substituted by an aryl group and phenyl group, e.g., tetrabutylammonium chloride, tetrabutyl ammonium bromide, tetrabutylammonium fluoride, tetrabutylammonium iodide, tetrabutyl ammonium hydroxide, tetrabutylammonium hydrogen sulfate, tributylmethylammonium chloride, tributylbenzylammonium chloride, tetraethylammonium chloride, tetramethyl ammonium chloride, tetrapentylammonium chloride, tetrapentylammonium bromide, tetrahexylammonium chloride, benzyldimethyloctylammonium chloride, methyltrihexyl ammonium chloride, benzylmethyloctadecanylammonium chloride, methyltridecanyl ammonium chloride, benzyltripropylammonium chloride, benzyltriethyl ammonium chloride, phenyltriethylammonium chloride and the like; phosphonium salts substituted with a residue such as a straight or branched alkyl group having 1 to about 18 carbon atoms, e.g., tetrabutylphosphonium chloride and the like; and pyridinium salts substituted with a straight or branched alkyl group having 1 to about 18 carbon atoms, e.g., 1-dodecanylpyridinium chloride and the like.

Specific phase transfer catalysts are tetrabutylammonium bromide, tetrabutylphosphonium bromide, tetrabutylammonium chloride, tetrabutylphosphonium chloride, benzyltriethylammonium chloride, tetrabutylammonium hydrogen sulfate, and more specifically tetrabutylammonium bromide.

In one embodiment, the base used in step-(a) is an organic or inorganic base. Specific organic bases are triethylamine, trimethylamine, N,N-diisopropylethylamine, N-methylmorpholine, N-methylpiperidine and 1,8-Diazabicycloundec-7-ene.

In another embodiment, the base is an inorganic base. Exemplary inorganic bases include, but are not limited to, hydroxides, alkoxides, and carbonates of alkali or alkaline earth metals, and ammonia. Specific inorganic bases are ammonia, sodium hydroxide, calcium hydroxide, magnesium hydroxide, potassium hydroxide, lithium hydroxide, sodium carbonate, potassium carbonate, lithium carbonate, sodium tert-butoxide, sodium isopropoxide and potassium tert-butoxide, and more specifically aqueous ammonia, sodium hydroxide, potassium hydroxide, sodium carbonate and potassium carbonate.

In one embodiment, the alkylation reaction in step-(a) is carried out at a temperature of about 0° C. to the reflux temperature of the solvent or solvent medium used, specifically at a temperature of about 20° C. to about 100° C., and more specifically at a temperature of about 30° C. to about 40° C. The reaction time may vary between about 10 hours to about 35 hours, specifically about 20 hours to about 32 hours, and more specifically about 22 hours to about 30 hours.

The reaction mass containing the 2-propylthio-pyrimidine-4,6-diol of formula IV obtained in step-(a) may be subjected to usual work up such as a washing, a filtration, an extraction, an evaporation, a pH adjustment, or a combination thereof. The reaction mass may be used directly in the next step to produce the 5-nitro-2-propylthiopyrimidine-4,6-diol of formula III, or the compound of formula IV may be isolated and then used in the next step.

In one embodiment, the 2-propylthio-pyrimidine-4,6-diol of formula IV formed in step-(a) is isolated as a solid from a suitable organic solvent by methods such as cooling, seeding, partial removal of the solvent from the solution, by adding an anti-solvent to the solution, evaporation, vacuum drying, or a combination thereof.

In another embodiment, the organic solvent used to isolate the 2-propylthio-pyrimidine-4,6-diol of formula IV is a non-polar solvent selected from the group consisting of an aliphatic ether, a hydrocarbon solvent, and mixtures thereof. Specifically, the non-polar solvent is selected from the group consisting of diethyl ether, diisopropyl ether, n-heptane, n-pentane, n-hexane, cyclohexane, and mixtures thereof. A most specific non-polar solvent is cyclohexane.

In one embodiment, the reaction mass containing the 2-propylthio-pyrimidine-4,6-diol of formula IV obtained in step-(a) is subjected to acidification by adjusting the pH to below 3, preferably 1 to 2, with an acid, followed by stirring the reaction mixture for at least 30 minutes, preferably for about 1 hour to about 15 hours, and isolating and/or recovering the product. The resulting wet cake is washed with water, followed by slurrying with the non-polar solvent selected from the group as described above and then recovering the product as a white powder. In one embodiment, the recovery of the product is accomplished by techniques such as filtration, filtration under vacuum, decantation, centrifugation, or a combination thereof. In another embodiment, the product is recovered by filtration employing a filtration media of, for example, a silica gel or celite.

Exemplary acids used for acidifying the reaction mass include, but are not limited to, acetic acid, nitric acid, hydrochloric acid, hydrobromic acid, sulfuric acid, phosphorus acid, aliphatic or aromatic sulphonic acids, propionic acid, and mixtures thereof; and a most specific acid is hydrochloric acid.

Exemplary second solvents used in step-(b) include, but are not limited to, a chlorinated hydrocarbon, an aliphatic acid, a sulfonic acid, an aliphatic or cyclic hydrocarbon, and mixtures thereof.

Specifically, the second solvent is selected from the group consisting of dichloromethane, dichloroethane, chloroform, carbon tetrachloride, acetic acid, propionic acid, butanoic acid, methane sulfonic acid, ethane sulfonic acid, sulfuric acid, n-pentane, n-hexane, n-heptane, cyclohexane, and mixtures thereof; and a most specific second solvent is acetic acid.

Exemplary nitrating agents used in step-(b) include, but are not limited to, nitric acid, nitric acid-sulfuric acid, silica supported sulfuric acid-nitric acid, and mixtures thereof and more specifically fuming nitric acid.

In one embodiment, the nitration reaction in step-(b) is carried out at a temperature of about 0° C. to about 50° C., specifically at a temperature of about 20° C. to about 40° C., and more specifically at a temperature of about 30° C. to about 35° C. The reaction time may vary between about 30 minutes to about 5 hours, specifically between about 1 hour to about 4 hours, and more specifically about 2 hours to about 3 hours. In another embodiment, the reaction mass may be quenched with water after completion of the reaction.

The reaction mass containing the 5-nitro-2-propylthiopyrimidine-4,6-diol of formula III obtained in step-(b) may be subjected to usual work up such as a washing, a filtration, an extraction, an evaporation, a pH adjustment, or a combination thereof. The reaction mass may be used directly in the next step to produce the 4,6-dichloro-5-nitro-2-(propylthio)pyrimidine of formula II, or the compound of formula III may be isolated and then used in the next step.

In one embodiment, the 5-nitro-2-propylthiopyrimidine-4,6-diol of formula III formed in step-(b) is isolated as a solid from a suitable organic solvent by methods such as cooling, seeding, partial removal of the solvent from the solution, by adding an anti-solvent to the solution, evaporation, vacuum drying, or a combination thereof.

Exemplary chlorinating reagents used in step-(c) include, but are not limited to, thionyl chloride, phosphorus oxychloride, phosphorus trichloride and phosphorus pentachloride. A most specific chlorinating reagent is phosphorus oxychloride.

The reaction in step-(c) is carried out in presence or absence of a third solvent. Exemplary third solvents include, but are not limited to, a hydrocarbon, a chlorinated hydrocarbon, and mixtures thereof. Specifically, the third solvent is selected from the group consisting of n-pentane, n-hexane, n-heptane, cyclohexane, toluene, xylene, methylene chloride, and mixtures thereof; and a more specific third solvent is toluene or cyclohexane.

In one embodiment, the reaction in step-(c) is carried out in the presence of excess chlorinating reagent which serves as a solvent and reactant. The excess chlorinating reagent is removed from the reaction mass after completion of the reaction by distillation or may be decomposed by adding water.

The chlorination reaction in step-(c) is carried out in the presence or absence of a base. In one embodiment, the chlorination reaction is carried out in the presence of aliphatic organic base. Exemplary aliphatic organic bases include, but are not limited to, triethyl amine, trimethylamine, N,N-diisopropylethylamine, N-methylmorpholine and N-methylpiperidine; and a most specific aliphatic organic base is N,N-diisopropylethylamine.

In one embodiment, the reaction in step-(c) is carried out at a temperature of about 25° C. to the reflux temperature of the solvent used, specifically at a temperature of about 60° C. to about 130° C., and more specifically at about 100° C. to about 120° C. In another embodiment, the reaction mass may be quenched with water after completion of the reaction.

The reaction mass containing the 4,6-dichloro-5-nitro-2-(propylthio)pyrimidine of formula II obtained in step-(c) may be subjected to usual work up such as a washing, a filtration, an extraction, an evaporation, a pH adjustment, or a combination thereof.

In one embodiment, the 4,6-dichloro-5-nitro-2-(propylthio)pyrimidine of formula II formed in step-(c) is isolated from a suitable organic solvent by the methods as described above.

In another embodiment, the organic solvent used to isolate the 4,6-dichloro-5-nitro-2-(propylthio)pyrimidine of formula II is selected from the group consisting of n-pentane, n-hexane, n-heptane, cyclohexane, toluene, xylene, methylene chloride, and mixtures thereof; and most specifically methylene chloride.

In another embodiment, the extracting solvent containing 4,6-dichloro-5-nitro-2-(propylthio)pyrimidine of formula II is further purified by treatment with silica gel having neutral pH and suitable particle size, anhydrous sodium sulfate, or a combination thereof. A specific mesh size of silica gel is 40-200 mesh, and more specifically 60-120 mesh.

Ticagrelor and pharmaceutically acceptable acid addition salts of ticagrelor can be prepared in high purity by using the substantially pure 4,6-dichloro-5-nitro-2-(propylthio)pyrimidine of formula II obtained by the methods disclosed herein, by known methods, for example, as per the processes described in U.S. Pat. Nos. 6,251,910 and 6,525,060.

The use of less hazardous, readily available, short process time and easy to handle reagents allows the process disclosed herein to be suitable for preparation of 4,6-dichloro-5-nitro-2-(propylthio)pyrimidine at lab scale and in commercial scale operations.

According to another aspect, there is provided a process for preparing 2-propylthio-pyrimidine-4,6-diol of formula IV:

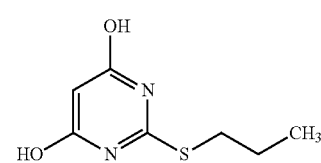

IV comprising:
reacting 2-thiobarbituric acid of formula V:

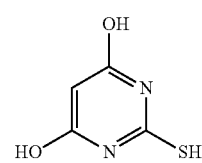

V with an alkylating agent of formula VI:

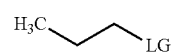

VI wherein LG is a leaving group selected from OH, Cl, Br, I, OSO$_3$ alkyl or aryl, OCOCH$_3$ and OP(O-alkyl)$_3$;
in the presence of a phase transfer catalyst and a base in a first solvent to produce the 2-propylthio-pyrimidine-4,6-diol of formula IV;
(or)
reacting an alkali metal salt of 2-thiobarbituric acid of formula V with the alkylating agent of formula VI in the presence of a base, optionally in the presence of a phase transfer catalyst, in the first solvent to produce the 2-propylthio-pyrimidine-4,6-diol of formula IV.

In one embodiment, the first solvent, the phase transfer catalyst and the base used in the alkylation reaction are, each independently, selected from the groups as described above.

In another embodiment, the alkali metal salt of 2-thiobarbituric acid of formula V used in the above reaction is sodium 2-thiobarbiturate.

In another embodiment, the alkylation reaction is carried out at a temperature and for a time period as described above.

According to another aspect, there is provided a process for preparing pure 2-propylthio-pyrimidine-4,6-diol of formula IV:

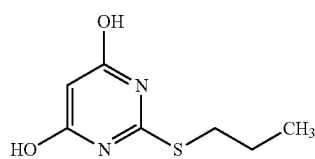

comprising:
a) reacting 2-thiobarbituric acid of formula V:

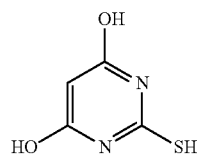

with an alkylating agent of formula VI:

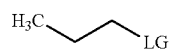

wherein LG is a leaving group selected from OH, Cl, Br, I, $OSO_3$ alkyl or aryl, $OCOCH_3$ and $OP(O\text{-alkyl})_3$;
in the presence of a phase transfer catalyst and a base in a first solvent to produce 2-propylthio-pyrimidine-4,6-diol of formula IV;
(or)
reacting an alkali metal salt of 2-thiobarbituric acid of formula V with the alkylating agent of formula VI in the presence of a base, optionally in the presence of a phase transfer catalyst, in the first solvent to produce the 2-propylthio-pyrimidine-4,6-diol of formula IV;
b) acidifying the reaction mass obtained in step-(a) by adjusting the pH to below 3 with an acid to produce a first slurry;
c) optionally, stirring the slurry obtained in step-(b) at a temperature below about 50° C. to produce a second slurry;
d) recovering the 2-propylthio-pyrimidine-4,6-diol from the first slurry obtained in step-(b) or the second slurry obtained in step-(c) as a solid;
e) suspending the solid obtained in step-(d) in a non-polar solvent to produce third slurry; and
f) isolating and/or recovering the substantially pure 2-propylthio-pyrimidine-4,6-diol from the third slurry.

The term "substantially pure 2-propylthio-pyrimidine-4,6-diol" refers to 2-propylthio-pyrimidine-4,6-diol having a total purity of greater than about 95%, specifically greater than about 98%, more specifically greater than about 99%, and still more specifically greater than about 99.5%. The purity is preferably measured by High Performance Liquid Chromatography (HPLC). For example, the purity of 2-propylthio-pyrimidine-4,6-diol obtained by the process disclosed herein is about 95% to about 99%, or about 98% to about 99.5%, as measured by HPLC.

In one embodiment, the first solvent, the phase transfer catalyst and the base used in step-(a) are, each independently, selected from the groups as described above.

In another embodiment, the alkali metal salt of 2-thiobarbituric acid of formula V used in step-(a) is sodium 2-thiobarbiturate.

In another embodiment, the alkylation reaction in step-(a) is carried out at a temperature and for a time period as described above.

In one embodiment, the pH of the reaction mass in step-(b) is adjusted to below 2.5, and specifically between 1 and 2.

Exemplary acids used for acidifying the reaction mass in step-(b) include, but are not limited to, acetic acid, nitric acid, hydrochloric acid, hydrobromic acid, sulfuric acid, phosphorus acid, aliphatic or aromatic sulphonic acids, propionic acid, and mixtures thereof; and a most specific acid is hydrochloric acid.

In one embodiment, the stirring in step-(c) is carried at a temperature of about 0° C. to about 40° C. for at least 30 minutes, and most specifically at a temperature of about 20° C. to about 35° C. for about 1 hour to about 15 hours.

In another embodiment, the recovering in steps-(d) and (f) is carried out by the methods as described above.

Exemplary non-polar solvents used in step-(e) include, but are not limited to, an aliphatic ether, a hydrocarbon solvent, and mixtures thereof. Specifically, the non-polar solvent is selected from the group consisting of diethyl ether, diisopropyl ether, n-heptane, n-pentane, n-hexane, cyclohexane, and mixtures thereof. A most specific non-polar solvent is cyclohexane.

The isolation of substantially pure 2-propylthio-pyrimidine-4,6-diol in step-(f) is carried out, for example, by cooling, seeding, partial removal of the solvent from the solution, by combining an anti-solvent with the solution, by substantial removal the solvent from the solution, concentrating the solution or distillation of the solvent under inert atmosphere, or a combination thereof.

In one embodiment, the isolation in step-(f) is carried out by cooling the third slurry while stirring at a temperature of below 30° C. for at least 15 minutes, specifically at about 0° C. to about 30° C. for about 20 minutes to about 20 hours, and more specifically at about 20° C. to about 30° C. for about 1 hour to about 10 hours.

The following examples are given for the purpose of illustrating the present disclosure and should not be considered as limitation on the scope or spirit of the disclosure.

EXAMPLES

Example 1

Preparation of 2-propylthio-pyrimidine-4,6-diol without using phase transfer catalyst 2-Thiobarbituric acid (100 g) was added to water (250 ml) under stirring. A solution of sodium hydroxide pellets or flakes (63.13 g) in water (147.35 ml) was added to the resulting mixture over a period of 15 to 20 minutes at 20-25° C. The resulting mass was stirred for 40 minutes at 20-25° C., followed by the addition of water (200 ml). The reaction temperature was raised to 30-35° C., followed by the addition of methanol (200 ml) and propyl iodide (123.36 g) under stirring at 30-35° C. The resulting reaction mixture was stirred for 30 hours at 30-35° C. The reaction was monitored by thin layer chromatography. After completion of reaction, the pH of the reaction mixture was then adjusted to less than 2.0 by the addition of dilute hydrochloric acid (prepared by mixing of 60 ml of concentrated hydrochloric acid with 140 ml of water). The resulting slurry was stirred for 15 hours and the product was isolated by filtration and washed successively with water (4×200 ml). The wet cake was slurried in cyclohexane (500 ml) at boiling temperature for 30 minutes, followed by cooling to 25-30° C. The product was isolated by filtration and washed with cyclohexane (200 ml). The wet product was dried under reduced pressure at 40-45° C. to produce 80 g of 2-propylthio-pyrimidine-4,6-diol as a white powder (Yield: 61.9%).

$^1$H-NMR (CDCl$_3$, δ): 0.91 (3H, t), 1.57 (2H, m), 3.02 (2H, t), 5.10 (1H,$), 11.71 (2H, bs); Mass [M-H]: 185.20.

Example 2

Preparation of 2-propylthio-pyrimidine-4,6-diol using phase transfer catalyst

2-Thiobarbituric acid (100 g) was added to the water (250 ml) under stirring, followed by the addition of a solution of sodium hydroxide pellets or flakes (63.13 g) in water (147.35 ml) over a period of 15 to 20 minutes at 20-25° C. The resulting mass was stirred for 40 minutes at 20-25° C., followed by the addition of water (200 ml). The reaction temperature was raised to 30-35° C., followed by addition of methanol (200 ml), propyl iodide (123.36 g) and tetrabutyl ammonium bromide (1.0 g) under stirring at 30-35° C. The resulting reaction mixture was stirred for 24 hours at 30-35° C. The reaction was monitored by thin layer chromatography. After completion of reaction, the pH of the reaction mixture was adjusted to less than 2.0 by the addition of dilute hydrochloric acid (prepared by mixing of 60 ml of concentrated hydrochloric acid with 140 ml of water). The resulting slurry was stirred for 15 hours, and the product was isolated by filtration and washed successively with water (4×200 ml) and cyclohexane (200 ml). The wet product was dried under reduced pressure at 40-45° C. to produce 85 g of 2-propylthio-pyrimidine-4,6-diol as a white powder (Yield: 65.7%; Purity by HPLC: 90.96 area-%).

Example 3

Preparation of sodium-2-thiobarbiturate

Dimethyl malonate (500 g) and thiourea (320 g) were added to methanol (1000 ml) under stirring, followed by heating at reflux temperature (60-65° C.). 30% w/w sodium methoxide solution in methanol (700 g) was slowly added to the hot reaction mass over a period of 30 minutes at reflux temperature (60-65° C.). After completion of addition, the reaction mass was stirred for 4 hours at reflux temperature (60-65° C.), followed by cooling to 25-30° C. The resulting slurry was stirred for 1 hour at 25-30° C., followed by isolation by filtration. The resulting wet material was washed with methanol (250 ml). The wet product was dried under reduced pressure at 50-55° C. to obtain the sodium-2-thiobarbiturate as an off white powder (521 g, HPLC purity: 99.68 area-%).

Example 4

Preparation of 2-propylthio-pyrimidine-4,6-diol

Sodium-2-thiobarbiturate (500 g) was added to the mixture of water (1500 ml) and methanol (1000 ml) under stirring, followed by the addition of an n-propyl bromide (407.3 g) at 25-30° C. The resulting mass was stirred for 15 minutes at 25-30° C., followed by the addition of an aqueous sodium hydroxide solution (132.44 g in 1500 ml of water) over a period of 6 to 7 hours, while maintaining the temperature between 25-30° C. The resulting reaction mixture was stirred for 22 hours at 25-30° C. After completion of the reaction, water (1000 ml) was added to the reaction mass, followed by pH adjustment to less than 2.0 by the addition of concentrated hydrochloric acid (337 ml). The resulting slurry was stirred for 1 hour and the product was isolated by filtration and washed successively with water (3×1000 ml). The wet product was dried under reduced pressure at 50-55° C. to produce 426.9 g of 2-propylthio-pyrimidine-4,6-diol as a white powder (Yield: 76.2%; HPLC purity: 94.87 area-%).

Example 5

Preparation of 5-nitro-2-propylthiopyrimidine-4,6-diol

Acetic acid (125 ml) and fuming nitric acid (42.5 ml) were placed in a clean and dry reaction assembly, followed by the addition of 2-propylthio-pyrimidine-4,6-diol (50 g) over a period of 60 minutes at 30-35° C. and with stirring for 1 hour. After completion of the reaction, monitored by TLC, the reaction mass was slowly added to water (250 ml) with maintaining the temperature at below 25° C. The resulting slurry was stirred for 1 hour at 20-25° C. The product was isolated by filtration and washed successively with water (3×100 ml). The wet product was dried under reduced pressure at 40-45° C. to produce 48.28 g of 5-nitro-2-propylthiopyrimidine-4,6-diol as a off-white powder (Purity by HPLC: 99.02 area-%).

$^1$H-NMR (DMSO, δ): 0.90 (3H, t), 1.60 (2H, m), 3.10 (2H, t); Mass [M-H]: 230.20.

Example 6

Preparation of 5-nitro-2-propylthiopyrimidine-4,6-diol

To a clean and dry reaction assembly containing acetic acid (1000 ml) was added fuming nitric acid (340 ml) over a period of 15 to 20 minutes, while maintaining the temperature between 25-30° C. 2-Propylthio-pyrimidine-4,6-diol (400 g) was added to the mixture over a period of 60 minutes at 25-30° C., followed by rinsing of flask with acetic acid (100 ml). The resulting mass was stirred for 1 hour at 25-30° C. After completion of the reaction, water (2400 ml) was added to the mass for 20 minutes at 25-30° C. The resulting slurry was stirred for 1 hour at 25-30° C. The product was isolated by filtration and washed successively with water (4×800 ml). The wet product was dried under reduced pressure at 50-55° C. to produce the 5-nitro-2-propylthiopyrimidine-4,6-diol as a off-white to yellow powder (375 g, HPLC purity: 99.06% by area).

Example 7

Preparation of 4,6-Dichloro-5-nitro-2-(propylthio)pyrimidine

5-Nitro-2-propylthiopyrimidine-4,6-diol (25 g) and phosphorus oxychloride (60 g) were placed in a clean and dry assembly, followed by slow addition of N,N-diisopropyl ethylamine (28.5 g) over a period of 20 to 30 minutes and maintaining the temperature at below 25° C. The resulting mixture was heated at 110-115° C. and maintained for 4 hours. The reaction was monitored by thin layer chromatography. After completion of the reaction, the reaction mass was slowly quenched into water (250 ml) while maintaining the temperature below 30° C., followed by stirring for 10 minutes. The reaction mass was extracted with dichloromethane (2×100 ml), followed by washing the organic layer with saturated sodium bicarbonate (75 ml), saturated sodium chloride solution (75 ml), and water (75 ml). The dichloromethane was evaporated at 50-55° C. under reduced pressure to produce 27 g of 4,6-dichloro-5-nitro-2-(propylthio)pyrimidine as an oil.

Example 8

Preparation of
4,6-Dichloro-5-nitro-2-(propylthio)pyrimidine

5-Nitro-2-propylthiopyrimidine-4,6-diol (50 g) and phosphorus oxychloride (175 gm) were placed in a clean and dry assembly, followed by slow addition of N,N-diisopropyl ethylamine (57.5 g) over a period of 20 to 30 minutes and maintaining the temperature at below 25° C. The resulting mixture was heated at 110-115° C. and maintained for 4 hours. The reaction was monitored by thin layer chromatography. After completion of the reaction, the reaction mass was slowly quenched into water (500 ml), while maintaining the temperature below 30° C., and followed by stirring for 10 minutes. The reaction mass was extracted with toluene (2×250 ml), followed by washing the organic layer with 3.33% w/v sodium bicarbonate (150 ml), 25.0% w/v sodium chloride solution (150 ml) and water (150 ml). The toluene layer was stirred with a silica gel neutral 60-120 mesh (50 g) for 30 minutes, followed by filtration through a hyflo bed. The hyflo bed was washed with toluene (150 ml) and combined with main filtrate. Combined toluene filtrate was evaporated at 50-55° C. under reduced pressure to produce 54.5 g of 4,6-dichloro-5-nitro-2-(propylthio)pyrimidine as an oil (Purity by HPLC: 97.81 area-%).

Example 9

Preparation of
4,6-Dichloro-5-nitro-2-(propylthio)pyrimidine

5-Nitro-2-propylthiopyrimidine-4,6-diol (100 g) and phosphorus oxychloride (350 g) were placed in a clean and dry assembly, followed by slow addition of N,N-diisopropyl ethylamine (115 g) over a period of 30 minutes, and maintaining the temperature at below 40° C. The resulting mixture was heated at 110-115° C. and maintained for 3 hours. The reaction was monitored by high performance liquid chromatography. After completion of the reaction, the reaction mass was cooled to 60° C., followed by the addition of toluene (250 ml). The resulting solution was evaporated under reduced pressure, followed by the removal of traces of phosphorus chloride with the addition of toluene (9250 ml), and evaporation. The resulting mass was diluted with toluene (500 ml), followed by slowly quenching into water (1000 ml), while maintaining the temperature at below 30° C. and then stirring for 10 minutes. The reaction mass was extracted two times with toluene (500 ml+300 ml), followed by washing the organic layer with 3.33% w/v sodium bicarbonate (300 ml), 25.0% w/v sodium chloride solution (300 ml). The toluene layer was stirred with a silica gel neutral 60-120 mesh (100 g) and sodium sulfate anhydrous (50 gm) for 30 minutes, followed by filtration through a hyflo bed. The hyflo bed was washed with toluene (2×100 ml) and washing was combined with main filtrate. The combined toluene filtrate was evaporated at 50-55° C. under reduced pressure to produce 116 g of 4,6-dichloro-5-nitro-2-(propylthio)pyrimidine as an oil (HPLC purity: 99.62% by area).

Example 10

Preparation of
4,6-Dichloro-5-nitro-2-(propylthio)pyrimidine

5-Nitro-2-propylthiopyrimidine-4,6-diol (200 gm), toluene (1000 ml) and phosphorus oxychloride (425.6 g) were placed in a clean and dry assembly, followed by the slow addition of N,N-diisopropyl ethylamine (230.0 g) over a period of 30 minutes, and maintaining the temperature at below 30° C. The resulting mixture was heated at 110-115° C., and maintained for 3 hours. After completion of the reaction, the reaction mass was cooled to 550° C., followed by distillation of a mixture of toluene and phosphorus oxychloride under reduced pressure. The traces of phosphorus chloride were removed with addition of toluene (500 ml), followed by evaporation. The resulting mass was diluted with toluene (1000 ml), followed by slowly quenching into water (2000 ml) while maintaining the temperature at below 30° C. and then stirring for 10 minutes. The reaction mass was extracted two times with toluene (1000 ml+600 ml), followed by washing the organic layer with 3.33% w/v sodium bicarbonate (600 ml), 25.0% w/v sodium chloride solution (600 ml). The toluene layer was stirred with silica gel neutral 60-120 mesh (200 g) and sodium sulfate anhydrous (100 g) for 30 minutes, followed by filtration through hyflo bed. The hyflo bed was washed with toluene (2×200 ml) and the washing was combined with main filtrate. Combined toluene filtrate was evaporated at 50-55° C. under reduced pressure to produce 233.5 g of 4,6-dichloro-5-nitro-2-(propylthio)pyrimidine as an oil (HPLC purity: 99.45% by area).

All ranges disclosed herein are inclusive and combinable. While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

We claim:
1. A process for preparing 4,6-dichloro-5-nitro-2-(propylthio)pyrimidine of formula II:

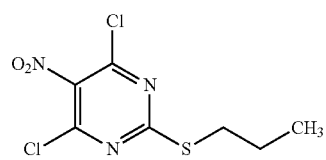

comprising:
a) reacting 2-thiobarbituric acid of formula V:

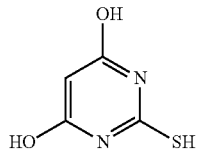

with an alkylating agent of formula VI:

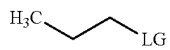

wherein LG is a leaving group and is Br;
in the presence of a phase transfer catalyst and a base in a first solvent to produce 2-propylthio-pyrimidine-4,6-diol of formula IV:

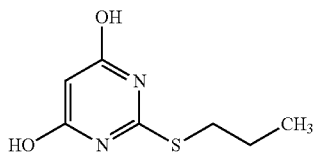

or
reacting an alkali metal salt of 2-thiobarbituric acid of formula V as a starting material with the alkylating agent of formula VI in the presence of a base, optionally in the presence of a phase transfer catalyst, in the first solvent to produce the 2-propylthio-pyrimidine-4,6-diol of formula IV;
b) nitrating the compound of formula IV with a nitrating agent in a second solvent to produce 5-nitro-2-propylthiopyrimidine-4,6-diol of formula III:

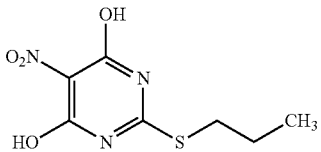

c) chlorinating the compound of formula III with a chlorinating agent in the presence of an aliphatic organic base, optionally in the presence of a third solvent, to produce substantially pure 4,6-dichloro-5-nitro-2-(propylthio)pyrimidine of formula II.

2. The process of claim 1, wherein the alkali metal salt of 2-thiobarbituric acid of formula V used in step-(a) is sodium 2-thiobarbiturate or potassium 2-thiobarbiturate; wherein the first solvent used in step-(a) is selected from the group consisting of water, methanol, ethanol, n-propanol, isopropanol, n-butanol, isobutanol, tert-butanol, amyl alcohol, hexanol, acetone, methylethyl ketone, methylisobutyl ketone, methyl tert-butyl ketone, acetonitrile, tetrahydrofuran, dioxane, diethyl ether, diisopropyl ether, monoglyme, diglyme, n-pentane, n-hexane, n-heptane, cyclohexane, toluene, xylene, N,N-dimethylformamide, N,N-dimethylacetamide, dimethylsulfoxide, and mixtures thereof; wherein the phase transfer catalyst used in step-(a) is selected from the group consisting of tetrabutylammonium chloride, tetrabutyl ammonium bromide, tetrabutylammonium fluoride, tetrabutylammonium iodide, tetrabutyl ammonium hydroxide, tetrabutylammonium hydrogen sulfate, tributylmethylammonium chloride, tributylbenzylammonium chloride, tetraethylammonium chloride, tetramethyl ammonium chloride, tetrapentylammonium chloride, tetrapentylammonium bromide, tetrahexylammonium chloride, benzyldimethyloctylammonium chloride, methyltrihexyl ammonium chloride, benzylmethyloctadecanylammonium chloride, methyltridecanyl ammonium chloride, benzyltripropylammonium chloride, benzyltriethyl ammonium chloride, phenyltriethylammonium chloride, tetrabutylphosphonium chloride and 1-dodecanylpyridinium chloride; and wherein the base used in step-(a) is selected from the group consisting of triethylamine, trimethylamine, N,N-diisopropylethylamine, N-methylmorpholine, N-methylpiperidine, 1,8-Diazabicycloundec-7-ene, ammonia, sodium hydroxide, calcium hydroxide, magnesium hydroxide, potassium hydroxide, lithium hydroxide, sodium carbonate, potassium carbonate, lithium carbonate, sodium tert-butoxide, sodium isopropoxide and potassium tert-butoxide.

3. The process of claim 2, wherein the alkali metal salt of 2-thiobarbituric acid of formula V is sodium 2-thiobarbiturate; wherein the first solvent is selected from the group consisting of water, methanol, ethanol, n-propanol, isopropanol, and mixtures thereof; wherein the phase transfer catalyst is selected from the group consisting of tetrabutylammonium bromide, tetrabutylphosphonium bromide, tetrabutylammonium chloride, tetrabutylphosphonium chloride, benzyltriethylammonium chloride and tetrabutylammonium hydrogen sulfate; and wherein the base is selected from the group consisting of aqueous ammonia, sodium hydroxide, potassium hydroxide, sodium carbonate and potassium carbonate.

4. The process of claim 1, wherein the second solvent used in step-(b) is selected from the group consisting of dichloromethane, dichloroethane, chloroform, carbon tetrachloride, acetic acid, propionic acid, butanoic acid, methane sulfonic acid, ethane sulfonic acid, sulfuric acid, n-pentane, n-hexane, n-heptane, cyclohexane, and mixtures thereof; wherein the nitrating agent used in step-(b) is selected from the group consisting of nitric acid, nitric acid-sulfuric acid, silica supported sulfuric acid-nitric acid, and mixtures thereof; wherein the chlorinating reagent used in step-(c) is selected from the group consisting of thionyl chloride, phosphorus oxychloride, phosphorus trichloride and phosphorus pentachloride; wherein the reaction in step-(c) is carried out in presence or absence of a third solvent selected from the group consisting of a hydrocarbon, a chlorinated hydrocarbon, and mixtures thereof; and wherein the chlorination reaction in step-(c) is carried out in the presence of an aliphatic organic base.

5. The process of claim 4, wherein the second solvent is acetic acid; wherein the nitrating agent used in step-(b) is fuming nitric acid; wherein the chlorinating reagent used in step-(c) is phosphorus oxychloride; wherein the third solvent is selected from the group consisting of n-pentane, n-hexane, n-heptane, cyclohexane, toluene, xylene, methylene chloride, and mixtures thereof; and wherein the aliphatic organic base used for chlorination reaction is selected from the group consisting of triethyl amine, trimethylamine, N,N-diisopropylethylamine, N-methylmorpholine and N-methylpiperidine.

6. The process of claim 4, wherein the alkylation reaction in step-(a) is carried out at a temperature of about 0° C. to the reflux temperature of the solvent or solvent medium used for about 10 hours to about 35 hours; wherein the reaction mass containing the 2-propylthio-pyrimidine-4,6-diol of formula IV obtained in step-(a) is subjected to acidification by adjusting the pH to below 3; wherein the nitration reaction in step-(b) is carried out at a temperature of about 0° C. to about 50° C. for about 30 minutes to about 5 hours; and wherein the reaction in step-(c) is carried out at a temperature of about 25° C. to the reflux temperature of the solvent used.

7. The process of claim 6, wherein the alkylation reaction in step-(a) is carried out at a temperature of about 20° C. to about 100° C. for about 20 hours to about 32 hours; wherein the acid used for acidifying the reaction mass obtained in step-(a) is selected from the group consisting of acetic acid, nitric acid, hydrochloric acid, hydrobromic acid, sulfuric acid, phosphorus acid, aliphatic or aromatic sulphonic acids, propionic acid, and mixtures thereof; wherein the nitration reaction in step-(b) is carried out at a temperature of about 20° C. to about 40° C. for about 1 hour to about 4 hours; and wherein the reaction in step-(c) is carried out at a temperature of about 60° C. to about 130° C.

8. The process of claim 1, wherein the 4,6-dichloro-5-nitro-2-(propylthio)pyrimidine of formula II obtained in step-(c) is isolated using a suitable organic solvent by cooling, seeding, partial removal of the solvent from the solution, by adding an anti-solvent to the solution, evaporation, vacuum drying, or a combination thereof; wherein the organic solvent used to isolate the 4,6-dichloro-5-nitro-2-(propylthio)pyrimidine of formula II is selected from the group consisting of n-pentane, n-hexane, n-heptane, cyclohexane, toluene, xylene, methylene chloride, and mixtures thereof; and wherein the 4,6-dichloro-5-nitro-2-(propylthio)pyrimidine of formula II obtained is further purified by treatment with silica gel having neutral pH and suitable particle size, anhydrous sodium sulfate, or a combination thereof.

9. A process for preparing 2-propylthio-pyrimidine-4,6-diol of formula IV:

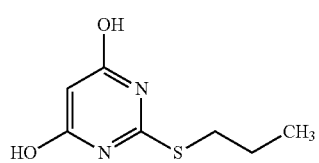

IV comprising:
reacting 2-thiobarbituric acid of formula V:

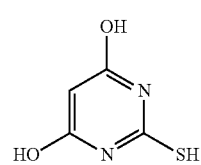

V with an alkylating agent of formula VI:

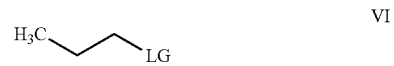

VI wherein LG is a leaving group and is Br;
in the presence of a phase transfer catalyst and a base in a first solvent to produce the 2-propylthio-pyrimidine-4,6-diol of formula IV;
or
reacting an alkali metal salt of 2-thiobarbituric acid of formula V as a starting material with the alkylating agent of formula VI in the presence of a base, optionally in the presence of a phase transfer catalyst, in the first solvent to produce the 2-propylthio-pyrimidine-4,6-diol of formula IV.

10. The process of claim 9, wherein the alkali metal salt of 2-thiobarbituric acid of formula V is sodium 2-thiobarbiturate or potassium 2-thiobarbiturate; wherein the first solvent is selected from the group consisting of water, methanol, ethanol, n-propanol, isopropanol, n-butanol, isobutanol, tert-butanol, amyl alcohol, hexanol, acetone, methylethyl ketone, methylisobutyl ketone, methyl tert-butyl ketone, acetonitrile, tetrahydrofuran, dioxane, diethyl ether, diisopropyl ether, monoglyme, diglyme, n-pentane, n-hexane, n-heptane, cyclohexane, toluene, xylene, N,N-dimethylformamide, N,N-dimethylacetamide, dimethylsulfoxide, and mixtures thereof; wherein the phase transfer catalyst is selected from the group consisting of tetrabutylammonium chloride, tetrabutyl ammonium bromide, tetrabutylammonium fluoride, tetrabutylammonium iodide, tetrabutyl ammonium hydroxide, tetrabutylammonium hydrogen sulfate, tributylmethylammonium chloride, tributylbenzylammonium chloride, tetraethylammonium chloride, tetramethyl ammonium chloride, tetrapentylammonium chloride, tetrapentylammonium bromide, tetrahexylammonium chloride, benzyldimethyloctylammonium chloride, methyltrihexyl ammonium chloride, benzylmethyloctadecanylammonium chloride, methyltridecanyl ammonium chloride, benzyltripropylammonium chloride, benzyltriethyl ammonium chloride, phenyltriethylammonium chloride, tetrabutylphosphonium chloride and 1-dodecanylpyridinium chloride; and wherein the base is selected from the group consisting of triethylamine, trimethylamine, N,N-diisopropylethylamine, N-methylmorpholine, N-methylpiperidine, 1,8-Diazabicycloundec-7-ene, ammonia, sodium hydroxide, calcium hydroxide, magnesium hydroxide, potassium hydroxide, lithium hydroxide, sodium carbonate, potassium carbonate, lithium carbonate, sodium tert-butoxide, sodium isopropoxide and potassium tert-butoxide.

11. The process of claim 10, wherein the alkali metal salt of 2-thiobarbituric acid of formula V is sodium 2-thiobarbiturate; wherein the first solvent is selected from the group consisting of water, methanol, ethanol, n-propanol, isopropanol, and mixtures thereof; wherein the phase transfer catalyst is selected from the group consisting of tetrabutylammonium bromide, tetrabutylphosphonium bromide, tetrabutylammonium chloride, tetrabutylphosphonium chloride, benzyltriethylammonium chloride and tetrabutylammonium hydrogen sulfate; and wherein the base is selected from the group consisting of aqueous ammonia, sodium hydroxide, potassium hydroxide, sodium carbonate and potassium carbonate.

12. A process for preparing pure 2-propylthio-pyrimidine-4,6-diol of formula IV:

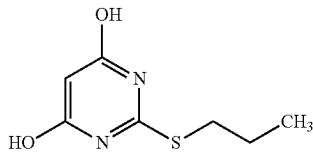

comprising:
a) reacting 2-thiobarbituric acid of formula V:

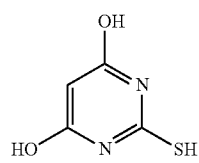

with an alkylating agent of formula VI:

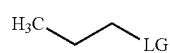

wherein LG is a leaving group and is Br;
in the presence of a phase transfer catalyst and a base in a first solvent to produce 2-propylthio-pyrimidine-4,6-diol of formula IV;
or
reacting an alkali metal salt of 2-thiobarbituric acid of formula V as a starting material with the alkylating agent of formula VI in the presence of a base, optionally in the presence of a phase transfer catalyst, in the first solvent to produce the 2-propylthio-pyrimidine-4,6-diol of formula IV;
b) acidifying the reaction mass obtained in step-(a) by adjusting the pH to below 3 with an acid to produce a first slurry;
c) optionally, stirring the slurry obtained in step-(b) at a temperature below about 50° C. to produce a second slurry;
d) recovering the 2-propylthio-pyrimidine-4,6-diol from the first slurry obtained in step-(b) or the second slurry obtained in step-(c) as a solid;
e) suspending the solid obtained in step-(d) in a non-polar solvent to produce third slurry; and
f) isolating and/or recovering the substantially pure 2-propylthio-pyrimidine-4,6-diol from the third slurry.

13. The process of claim 12, wherein the alkali metal salt of 2-thiobarbituric acid of formula V used in step-(a) is sodium 2-thiobarbiturate or potassium 2-thiobarbiturate; wherein the first solvent used in step-(a) is selected from the group consisting of water, methanol, ethanol, n-propanol, isopropanol, n-butanol, isobutanol, tert-butanol, amyl alcohol, hexanol, acetone, methylethyl ketone, methylisobutyl ketone, methyl tert-butyl ketone, acetonitrile, tetrahydrofuran, dioxane, diethyl ether, diisopropyl ether, monoglyme, diglyme, n-pentane, n-hexane, n-heptane, cyclohexane, toluene, xylene, N,N-dimethylformamide, N,N-dimethylacetamide, dimethylsulfoxide, and mixtures thereof; wherein the phase transfer catalyst used in step-(a) is selected from the group consisting of tetrabutylammonium chloride, tetrabutyl ammonium bromide, tetrabutylammonium fluoride, tetrabutylammonium iodide, tetrabutyl ammonium hydroxide, tetrabutylammonium hydrogen sulfate, tributylmethylammonium chloride, tributylbenzylammonium chloride, tetraethylammonium chloride, tetramethyl ammonium chloride, tetrapentylammonium chloride, tetrapentylammonium bromide, tetrahexylammonium chloride, benzyldimethyloctylammonium chloride, methyltrihexyl ammonium chloride, benzylmethyloctadecanylammonium chloride, methyltridecanyl ammonium chloride, benzyltripropylammonium chloride, benzyltriethyl ammonium chloride, phenyltriethylammonium chloride, tetrabutylphosphonium chloride and 1-dodecanylpyridinium chloride; and wherein the base used in step-(a) is selected from the group consisting of triethylamine, trimethylamine, N,N-diisopropylethylamine, N-methylmorpholine, N-methylpiperidine, 1,8-Diazabicycloundec-7-ene, ammonia, sodium hydroxide, calcium hydroxide, magnesium hydroxide, potassium hydroxide, lithium hydroxide, sodium carbonate, potassium carbonate, lithium carbonate, sodium tert-butoxide, sodium isopropoxide and potassium tert-butoxide.

14. The process of claim 12, wherein the pH of the reaction mass in step-(b) is adjusted to below 2.5; wherein the acid used for acidifying the reaction mass in step-(b) is selected from the group consisting of acetic acid, nitric acid, hydrochloric acid, hydrobromic acid, sulfuric acid, phosphorus acid, aliphatic or aromatic sulphonic acids, propionic acid, and mixtures thereof; wherein the stirring in step-(c) is carried at a temperature of about 0° C. to about 40° C. for at least 30 minutes; wherein the non-polar solvents used in step-(e) is selected from the group consisting of diethyl ether, diisopropyl ether, n-heptane, n-pentane, n-hexane, cyclohexane, and mixtures thereof; and wherein the isolation of substantially pure 2-propylthio-pyrimidine-4,6-diol in step-(f) is carried out by cooling, seeding, partial removal of the solvent from the solution, by combining an anti-solvent with the solution, by substantial removal the solvent from the solution, concentrating the solution or distillation of the solvent under inert atmosphere, or a combination thereof.

15. The process of claim 14, wherein the pH of the reaction mass in step-(b) is adjusted between 1 and 2; wherein the acid used for acidifying the reaction mass in step-(b) is hydrochloric acid; wherein the stirring in step-(c) is carried at a temperature of about 20° C. to about 35° C. for about 1 hour to about 15 hours; wherein the non-polar solvents used in step-(e) is cyclohexane; and wherein the isolation in step-(f) is carried out by cooling the third slurry while stirring at a temperature of about 20° C. to about 30° C. for about 1 hour to about 10 hours.

16. A method for preparing ticagrelor or a pharmaceutically acceptable salt thereof comprising 4,6-dichloro-5-nitro-2-(propylthio)pyrimidine of formula II:

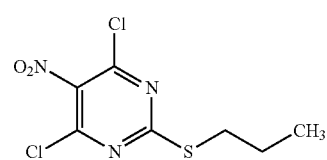

as an intermediate wherein the 4,6-dichloro-5-nitro-2-(propylthio)pyrimidine of formula II is prepared by a process comprising:

a) reacting 2-thiobarbituric acid of formula V:

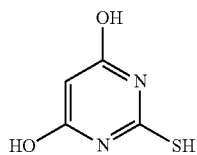

V with an alkylating agent of formula VI:

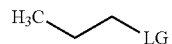

VI wherein LG is a leaving group and is Br;
in the presence of a phase transfer catalyst and a base in a first solvent to produce 2-propylthio-pyrimidine-4,6-diol of formula IV;

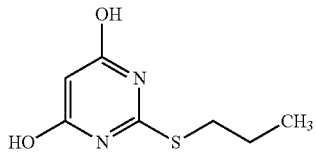

IV (or)

reacting an alkali metal salt of 2-thiobarbituric acid of formula V as a starting material with the alkylating agent of formula VI in the presence of a base, optionally in the presence of a phase transfer catalyst, in the first solvent to produce the 2-propylthio-pyrimidine-4,6-diol of formula IV;

(b) nitrating the compound of formula IV with a nitrating agent in a second solvent to produce 5-nitro-2-propylthiopyrimidine-4,6-diol of formula III;

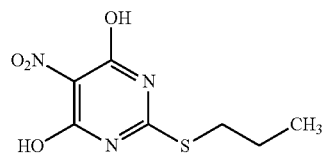

III (c) chlorinating the compound of formula III with a chlorinating agent in the presence of an aliphatic organic base, optionally in the presence of a third solvent, to produce substantially pure 4,6-dichloro-5-nitro-2-(propylthio)pyrimidine of formula II.

* * * * *